United States Patent
Jia et al.

(10) Patent No.: US 11,971,349 B1
(45) Date of Patent: Apr. 30, 2024

(54) COMBINED OXYGEN, NITROGEN AND HYDROGEN JOINT DETERMINATION DEVICE AND METHOD BASED ON THERMAL CONDUCTIVITY-INFRARED TECHNIQUE

(71) Applicants: NCS Testing Technology CO., LTD, Beijing (CN); NCS Jiangsu Testing Technology Co., Ltd., Jiangsu (CN)

(72) Inventors: Yunhai Jia, Beijing (CN); Xuehua Wang, Jiangsu (CN); Liangjing Yuan, Beijing (CN); Danyang Zhi, Beijing (CN); Runpeng Wang, Jiangsu (CN); Xiaoke Hao, Beijing (CN); Zhenning Wu, Beijing (CN); Wang Chen, Beijing (CN); Zhaodong Guo, Beijing (CN); Xinyang Dong, Jiangsu (CN)

(73) Assignees: NCS Testing Technology CO., LTD, Beijing (CN); NCS Jiangsu Testing Technology Co., Ltd., Suzhou (CN)

( * ) Notice: Subject to any disclaimer, the term of this patent is extended or adjusted under 35 U.S.C. 154(b) by 0 days.

(21) Appl. No.: 18/498,938

(22) Filed: Oct. 31, 2023

(30) Foreign Application Priority Data

Apr. 20, 2023 (CN) .......................... 202310424543.5

(51) Int. Cl.
*G01N 21/3504* (2014.01)
*G01N 1/40* (2006.01)
*G01N 1/44* (2006.01)

(52) U.S. Cl.
CPC ....... *G01N 21/3504* (2013.01); *G01N 1/4077* (2013.01); *G01N 1/44* (2013.01); *G01N 2001/4088* (2013.01)

(58) Field of Classification Search
CPC .... G01N 21/3504; G01N 1/4077; G01N 1/44; G01N 2001/4088
See application file for complete search history.

(56) References Cited

U.S. PATENT DOCUMENTS

2022/0244176 A1* 8/2022 Inoue ................. G01N 21/3504

FOREIGN PATENT DOCUMENTS

| CN | 114486797 A | 5/2022 |
|----|-------------|--------|
| DE | 102014012914 A1 | 3/2016 |

\* cited by examiner

*Primary Examiner* — Jennifer Wecker (57) ABSTRACT

The present invention discloses a combined oxygen, nitrogen and hydrogen joint determination device and method based on thermal conductivity-infrared technique. In the device, a melting and extraction system comprises a carrier gas introduction pipeline, a chamber valve, an impulse furnace and a dust filter; an analytical gas transmission system comprises a flush valve, a bypass valve, a mass flowmeter and a first switching valve; a signal detection system comprises an infrared cell, an analysis purification reagent tube and a thermal conductivity cell; and a signal analysis system comprises a controller and a processor. The present invention realizes different joint determination modes by switching different gas paths, which can meet different determination requirements of different users.

6 Claims, 3 Drawing Sheets

COMBINED OXYGEN, NITROGEN AND HYDROGEN JOINT DETERMINATION DEVICE AND METHOD BASED ON THERMAL CONDUCTIVITY-INFRARED TECHNIQUE

CROSS-REFERENCE TO RELATED APPLICATIONS

This application claims priority of Chinese Patent Application No. 202310424543.5, filed on Apr. 20, 2023, the entire contents of which are incorporated herein by reference.

TECHNICAL FIELD

The present invention relates to the technical field of gas element analysis in metal and alloy materials, in particular to a combined oxygen, nitrogen and hydrogen joint determination device and method based on thermal conductivity-infrared technique.

BACKGROUND

Oxygen, nitrogen and hydrogen gas elements have a very important effect on the properties of metal and alloy materials. The inclusion of oxygen and the "hydrogen embrittlement" phenomenon seriously reduce the plasticity of the materials, resulting in a sharp increase in the brittleness, which leads to deterioration of the mechanical properties, causing fracture accidents. An appropriate amount of nitrogen can improve the plasticity and stability of alloys, but the impact toughness of the metal material will be reduced in excessive amount, resulting in "blue brittleness". Therefore, the content of oxygen, nitrogen and hydrogen needs to be accurately determined in the processing and smelting procedure of the materials and the quality control of finished products.

The hydrogen content in metal and alloy materials is usually determined by an impulse heating inert gas fusion thermal conductivity (TC) method or infrared (IR) absorption method on two different devices. The TC method is to determine $H_2$ released from a molten sample by high-sensitivity thermistor wires to realize measurement of the hydrogen content in materials; and the core determination unit for the TC method is the TC cell, which adopts a Wheatstone bridge structure, the analysis arm is balanced with the reference arm when no sample gas passes through, and the balance is broken when the formed sample gas is carried by the carrier gas into the analysis arm, producing signal output directly proportional to the concentration of the sample gas. The traditional hydrogen analyzer for the impulse heating inert gas fusion TC method can determine hydrogen content in the full range, with the measurement principle shown in FIG. 1. $H_2$ released by sample melting in the impulse furnace is carried by the carrier gas to enter the TC cell after dust filtration and analysis purification, and finally subjected to signal processing to supply the analysis result.

Figure 2:
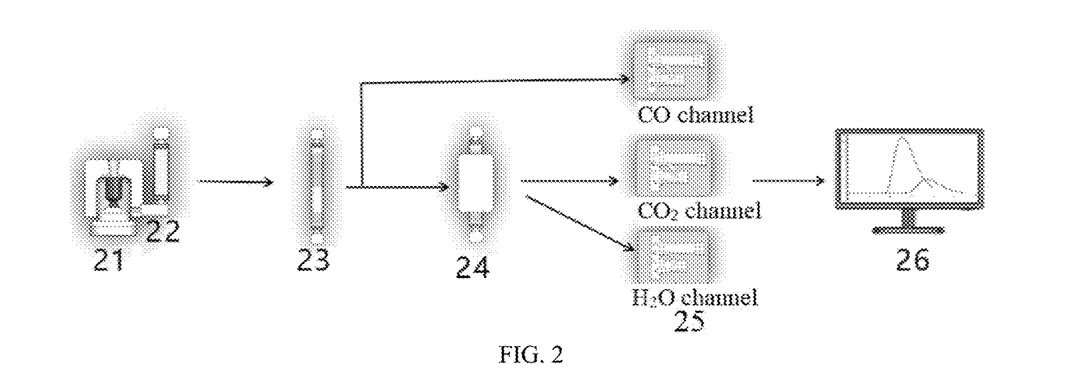
FIG. 2 is a schematic diagram of hydrogen or oxygen determination by the traditional IR absorption method.

The IR absorption method for hydrogen determination is to convert the $H_2$ released from the molten sample into $H_2O$ vapor, and then determine the hydrogen content in the material through the absorption of $H_2O$ vapor molecules at a specific IR band (6.5 μm). The core determination unit for the IR absorption method is the IR cell, and the basic structure thereof comprises an IR light source, a chopper, an optical path channel and a pyroelectric detector. The forming gas to be determined, such as $H_2O$ vapor molecules, results in variation in signals of the pyroelectric detector after absorbing IR ray with certain intensity, the amount of variation has a certain functional relationship with the content of the component to be determined, and the hydrogen content in the sample is calculated by analysis software. The measurement principle of the traditional hydrogen analyzer for the impulse heating inert gas fusion IR absorption method is shown in FIG. 2, $H_2$ released by sample melting in the impulse furnace is carried by the carrier gas to enter the converter after dust filtration and analysis purification so as to form a component to be determined, $H_2O$ vapor molecules, and the hydrogen content is determined through the $H_2O$ channel of the IR cell.

The IR absorption spectrum peak of the $H_2O$ vapor molecules is not intensive, and has more interference, but is relatively appropriate at the wavelength of 6.5 μm. The TC method uses high-purity $N_2$ as the carrier gas, the gas TC coefficients of $H_2$ and $N_2$ are quite different, and TC signals are very sensitive, which theoretically determines that the IR absorption method is not as sensitive as the TC method in the determination of the ultra-low content (≤3 μg/g). $H_2O$ vapor is prone to condensation in the range of high content (≥1000 μg/g) due to the influence of saturated vapor pressure, which leads to measurement errors in the IR absorption method. For the above reasons, the IR absorption method is generally suitable for determination of hydrogen in the medium and low content, i.e., the measurement range of 3 μg/g-1000 μg/g, while the TC method is suitable for determination in the full range. However, the IR absorption method can realize joint determination of hydrogen together with oxygen and nitrogen, which will provide higher determination efficiency. Therefore, how to realize combined application of the TC method and the IR absorption method in determination of oxygen, nitrogen and hydrogen gas elements has become a problem to be urgently solved.

SUMMARY

The purpose of the present invention is to provide a combined oxygen, nitrogen and hydrogen joint determination device and method based on thermal conductivity-infrared technique, a melting and extraction system and an analytical gas transmission system which are used in common are arranged for an infrared (IR) cell and a thermal conductivity (TC) cell to realize joint application of the IR absorption method and the TC method, different joint determination modes are realized by switching different gas paths, and only one device can realize the combination of multiple joint determination modes of oxygen, nitrogen and hydrogen, which meets different determination requirements of different users and saves the device cost, with ingenious design and simple and convenient operation.

To achieve the above purpose, the present invention provides the following solution:

A combined oxygen, nitrogen and hydrogen joint determination device based on thermal conductivity-infrared technique, comprising a melting and extraction system, an analytical gas transmission system, a signal detection system and a signal analysis system;

The melting and extraction system comprises a carrier gas introduction pipeline, a chamber valve, an impulse furnace and a dust filter communicated in sequence, wherein the carrier gas introduction pipeline is connected with at least two intake tubes for introducing different carrier gases;

The analytical gas transmission system comprises a flush valve, a bypass valve, a mass flowmeter and a first switching valve communicated in sequence, wherein the flush valve is communicated with the dust filter, the bypass valve is communicated with the chamber valve, the first switching valve is respectively connected with a converter and a second switching valve, the converter is communicated with the second switching valve, the analytical gas transmission system also comprises a reference valve and a needle valve, the reference valve is communicated with the chamber valve, and the needle valve is communicated with the reference valve;

The signal detection system comprises an IR cell, an analysis purification reagent tube and a TC cell communicated in sequence, wherein the IR cell is communicated with the second switching valve, and the TC cell is communicated with the needle valve;

The signal analysis system comprises a controller and a signal processor, wherein the controller is electrically connected with the signal processor, and the controller is electrically connected with the IR cell and the TC cell respectively; and the chamber valve, the flush valve, the bypass valve, the first switching valve, the second switching valve, the reference valve and the needle valve are all electrically controlled valves and are electrically connected with the controller respectively, and the controller realizes the opening and closing of different gas paths by controlling the opening and closing of different electrically controlled valves so as to realize joint determination modes of different gases.

Further, the carrier gas introduction pipeline comprises an intake switching valve, a carrier gas valve, a purifying furnace and a carrier gas purification reagent tube connected in sequence, wherein the carrier gas purification reagent tube is communicated with the chamber valve, and the intake switching valve is connected with at least two intake tubes for introducing different carrier gases.

Further, two intake tubes are arranged: a first air tube and a second air tube, wherein high-purity He is introduced into the first air tube as a carrier gas, and high-purity $N_2$ is introduced into the second air tube as a carrier gas.

Further, the intake tube is provided with a pressure relief valve.

Further, the intake switching valve and the carrier gas valve are electrically controlled valves and are electrically connected with the controller respectively, and the controller is communicated with different intake tubes by controlling the intake switching valve so as to realize introduction switching of different carrier gases.

The present invention also provides a combined oxygen, nitrogen and hydrogen joint determination method based on thermal conductivity-infrared technique, which is applied in the above combined oxygen, nitrogen and hydrogen joint determination device based on thermal conductivity-infrared technique, comprising the following steps:

A sample of metal or alloy material is put into the impulse furnace to release oxygen, nitrogen and hydrogen as CO, $N_2$ and $H_2$ molecules as analytical gases;

The carrier gas introduction pipeline is controlled to introduce high-purity He or high-purity $N_2$ as a carrier gas;

One branch of the introduced carrier gas enters the TC cell through the reference valve and the needle valve as the reference gas, and the other branch enters the chamber valve. When the sample is analyzed in the working state, the carrier gas is blown into the impulse furnace to carry the analytical gas released from the molten sample into the dust filter;

The analytical gas passing through the dust filter enters the flush valve, and the flush valve is opened at the degassing stage at the beginning of the analysis to exhaust waste gases; and after degassing, the analytical gas containing components to be determined passes through the bypass valve and the mass flowmeter in sequence;

When high-purity He is introduced as the carrier gas, the analytical gas is carried by the carrier gas to enter the IR cell through the first switching valve, the converter and the second switching valve in sequence and then enter the TC cell through the analysis purification reagent tube to realize O/N joint determination, N/H joint determination and O/N/H joint determination, wherein oxygen and hydrogen are determined by the IR absorption method, and nitrogen is determined by the TC method;

When high-purity $N_2$ is introduced as the carrier gas, the analytical gas is carried by the carrier gas to enter the IR cell through the second switching valve and then enter the TC cell through the analysis purification reagent tube to realize the O/H joint determination mode, wherein oxygen is determined by the IR absorption method, and hydrogen is determined by the TC method.

Further, the mass flowmeter is a mass flow controller MFC which adopts an He parameter mode in O/N, N/H and O/N/H joint determination modes and adopts an Ar parameter mode in the O/H joint determination mode.

According to specific embodiments provided by the present invention, the present invention discloses the following technical effects: the present invention provides the combined oxygen, nitrogen and hydrogen joint determination device and method based on thermal conductivity-infrared technique, wherein the device comprises a melting and extraction system, an analytical gas transmission system, a signal detection system and a signal analysis system; a melting and extraction system and an analytical gas transmission system which are used in common are arranged to realize the transmission of the analytical gas for the IR cell and the TC cell to realize joint application of the IR absorption method and the TC method, different gas paths can be opened by controlling the combined opening and closing of different valves, and different joint determination modes are realized by introducing different carrier gases, for example, when high-purity He is used as the carrier gas, O/N joint determination, N/H joint determination and O/N/H joint determination can be realized, oxygen and hydrogen are determined by the IR absorption method, and nitrogen is determined by the TC method; and when high-purity $N_2$ is used as the carrier gas, O/H joint determination can be realized, oxygen is determined by the IR absorption method, and hydrogen is determined by the TC method. The present invention realizes joint application of the IR absorption method and the TC method on one device, and realizes combined determination of different joint determination modes of oxygen, nitrogen and hydrogen on one device, the user can conduct flexible configuration according to different actual requirements such as the type and content range of determined elements, without the need to purchase additional instruments, and one device can meet diversified determination requirements, saving the production cost; and the automatic control of different valves and the switching of gas paths and parameters for joint determination modes of different elements are ingenious in design and convenient in operation.

DESCRIPTION OF DRAWINGS

To more clearly describe the technical solutions in the embodiments of the present invention or in prior art, the drawings required to be used in the embodiments will be simply presented below. Apparently, the drawings in the following description are merely some embodiments of the present invention, and for those skilled in the art, other drawings can also be obtained according to these drawings without contributing creative labor.

REFERENCE SIGNS 11. impulse furnace; 12. dust filter; 13. converter; 14. TC cell; and 15. signal processor;

21. impulse furnace; 22. dust filter; 23. analysis purification reagent tube; 24. converter; 25. IR cell; and 26. signal processor;

31. He pressure relief valve; 32. N2 pressure relief valve; 33. intake switching valve; 34. carrier gas valve; 35. purifying furnace; 36. carrier gas purification reagent tube; 37. chamber valve; 38. impulse furnace; 39. dust filter; 310. reference valve; 311. bypass valve; 312. flush valve; 313. mass flowmeter; 314. needle valve; 315. first switching valve; 316. second switching valve; 317. converter; 318. IR cell; 319. analysis purification reagent tube; 320. TC cell; 321. controller; and 322. signal processor.

DETAILED DESCRIPTION

The technical solutions in the embodiments of the present invention will be clearly and fully described below in combination with the drawings in the embodiments of the present invention. Apparently, the described embodiments are merely part of the embodiments of the present invention, not all of the embodiments. Based on the embodiments in the present invention, all other embodiments obtained by those ordinary skilled in the art without contributing creative labor will belong to the protection scope of the present invention.

Figure 1:
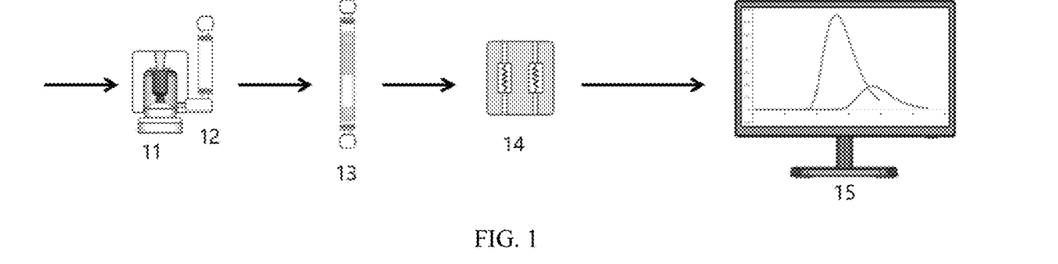
FIG. 1 is a schematic diagram of hydrogen or nitrogen determination by the traditional TC method.

The nitrogen content in metal and alloy materials is usually determined by an impulse heating inert gas fusion thermal conductivity (TC) method, and nitrogen in the sample is determined as $N_2$ molecules through the TC cell. FIG. 1 is a schematic diagram of hydrogen or nitrogen determination by the traditional TC method. The carrier gas passes through the impulse furnace 11 and the dust filter 12, the sample is dropped into a degassed high-temperature graphite crucible from the feeding port of the impulse furnace 11, hydrogen or nitrogen in the sample is released as atoms, and then the atoms are combined to form $H_2$ molecules or $N_2$ molecules. The measurement principle of the nitrogen analyzer for the traditional impulse heating inert gas fusion TC method is shown in FIG. 1, $N_2$ released by sample melting in the impulse furnace 11 is carried by the carrier gas to enter the TC cell 14 after dust filtration and analysis purification, and finally subjected to signal processing to obtain the analysis result.

The oxygen content in metal and alloy materials is usually determined by an impulse heating inert gas fusion IR absorption method, and oxygen in the sample can be determined by determining the IR absorption peak of CO molecules at 4.5 μm, or determined by further oxidation of CO molecules into $CO_2$ molecules at the IR absorption peak at 4.2 μm. FIG. 2 is a schematic diagram of hydrogen or oxygen determination by the traditional IR absorption method. The carrier gas passes through the impulse furnace 21 and the dust filter 22, the sample is dropped into a degassed high-temperature graphite crucible from the feeding port of the impulse furnace 21, hydrogen in the sample is released as atoms, the atoms are combined to form $H_2$ and then react with CuO in a high-temperature (500° C.) converter 13 to form $H_2O$ vapor, and the $H_2O$ vapor is carried by the carrier gas into the IR cell provided with an $H_2O$ determination channel and then subjected to signal amplification to obtain the hydrogen analysis result. The measurement principle of the traditional oxygen analyzer for the impulse heating inert gas fusion IR absorption method is shown in FIG. 2, and when the IR cell 25 uses a CO channel to determine the oxygen content, the converter 24 is not required. When the IR cell 25 uses a $CO_2$ channel to determine the oxygen content, the converter 24 is required.

Oxygen in the sample reacts with carbon in the graphite crucible at high temperatures (≥1000° C.) to form CO molecules due to excess carbon, and the CO molecules are directly carried by the carrier gas into the IR cell provided with a CO determination channel and then subjected to signal amplification to obtain the oxygen analysis result. The formed CO molecules react with CuO in the high-temperature (500° C.) converter to form $CO_2$ molecules, and the $CO_2$ molecules are carried by the carrier gas into the IR cell provided with a $CO_2$ determination channel and then subjected to signal amplification to obtain the oxygen analysis result.

The purpose of the present invention is to provide a combined oxygen, nitrogen and hydrogen joint determination device and method based on thermal conductivity-infrared technique, relating to the sample melting system, the TC determination technology, the IR absorption determination technology, the analytical gas transmission switching technology and the analysis software control technology, and to realize the integration of O/N, O/H, N/H and O/N/H joint determination technologies on one device, which replaces the original need for multiple devices to complete the joint determination of elements. For O/N joint determination, high-purity He is selected as the carrier gas, oxygen is determined by the $CO_2$ determination channel in the IR cell, and nitrogen is determined by the TC cell; for O/H joint determination, high-purity $N_2$ is selected as the carrier gas, oxygen is determined by the CO determination channel in the IR cell, and hydrogen is determined by the TC cell; for N/H joint determination, high-purity He is selected as the carrier gas, nitrogen is determined by the TC cell, and hydrogen is determined by the $H_2O$ determination channel in the IR cell; and for O/N/H joint determination, high-purity He is selected as the carrier gas, oxygen is determined by the $CO_2$ determination channel in the IR cell, nitrogen is determined by the TC cell, and hydrogen is determined by the $H_2O$ determination channel in the IR cell. The present invention uses a sample melting and extraction system and a signal detection system of one device, and the controller and the signal processor 15, 26 can control the switching of the analytical gas transmission paths for joint determination modes of different elements through the software algorithm system, which also can be realized through one-click operation in the method setup of the software, so the operation is simple and fast.

To make the above-mentioned purpose, features and advantages of the present invention more clear and understandable, the present invention will be further described below in detail in combination with the drawings and specific embodiments.

Figure 3:
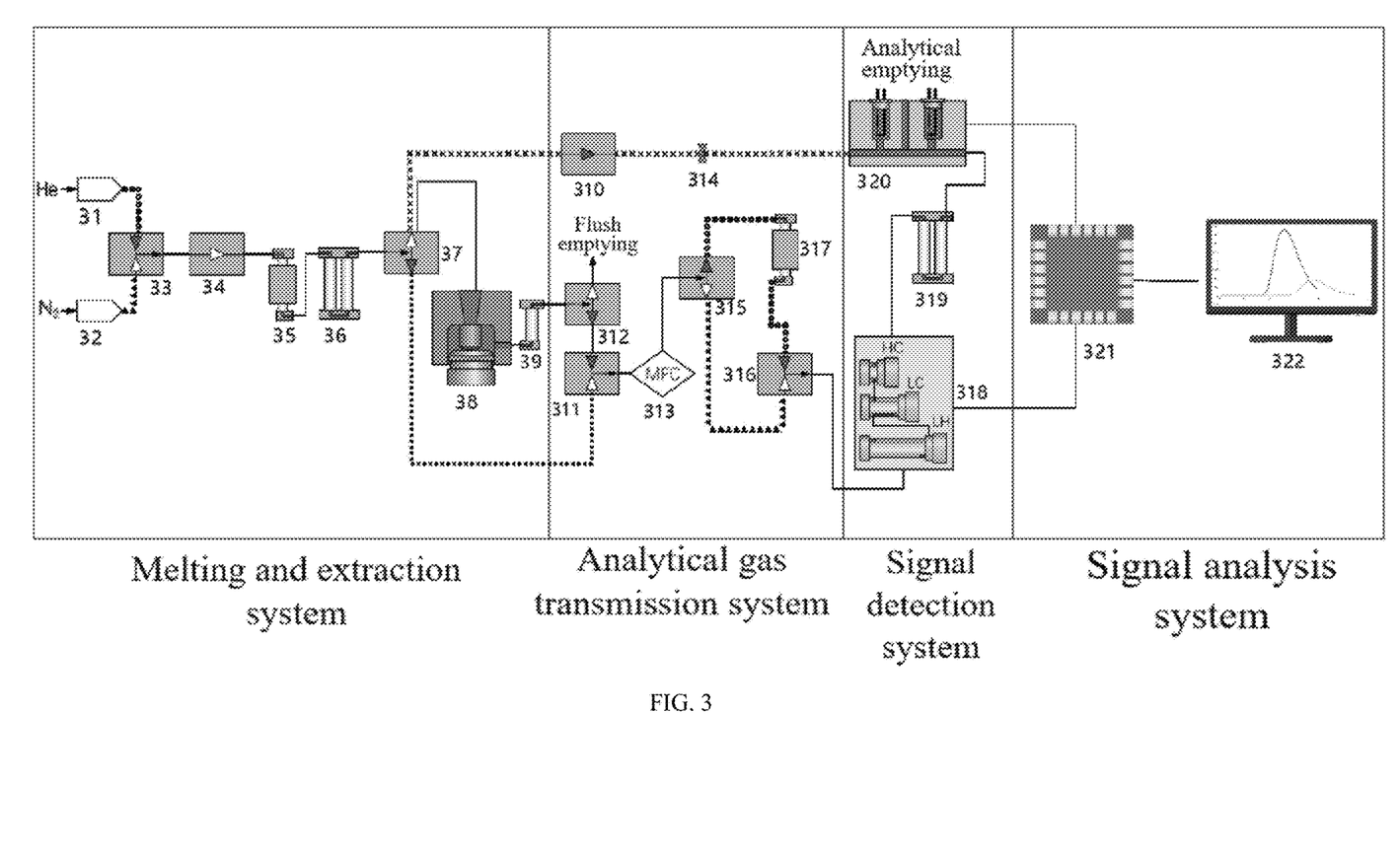
FIG. 3 is a structural schematic diagram of communication of a combined oxygen, nitrogen and hydrogen joint determination device based on thermal conductivity-infrared technique provided by the present invention.

As shown in FIG. 3, the combined oxygen, nitrogen and hydrogen joint determination device based on thermal conductivity-infrared technique provided by the present invention comprises a melting and extraction system, an analytical gas transmission system, a signal detection system and a signal analysis system;

The melting and extraction system comprises an intake switching valve 33, a carrier gas valve 34, a purifying furnace 35, a carrier gas purification reagent tube 36, a chamber valve 37, an impulse furnace 38 and a dust filter 39 communicated in sequence; and the intake switching valve 33 is connected with at least two intake tubes for introducing different carrier gases. Exemplarily, two intake tubes are arranged: a first air tube and a second air tube, wherein high-purity He is introduced into the first air tube as a carrier gas, and high-purity $N_2$ is introduced into the second air tube as a carrier gas. The first air tube is provided with an He pressure relief valve 31, and the second air tube is provided with an $N_2$ pressure relief valve 32;

The analytical gas transmission system comprises a flush valve 312, a bypass valve 311, a mass flowmeter 313 and a first switching valve 315 communicated in sequence, wherein the flush valve 312 is communicated with the dust filter 39, the bypass valve 311 is communicated with the chamber valve 37, the first switching valve 315 is respectively connected with a converter and a second switching valve 316, the converter 317 is communicated with the second switching valve 316, the analytical gas transmission system also comprises a reference valve 310 and a needle valve 314, the reference valve 310 is communicated with the chamber valve 37, and the needle valve 314 is communicated with the reference valve 310;

The signal detection system comprises an IR cell 318, an analysis purification reagent tube 23, 319 and a TC cell 320 communicated in sequence, wherein the IR cell 318 is communicated with the second switching valve 316, and the TC cell 320 is communicated with the needle valve 314;

The signal analysis system comprises a controller 321 and a signal processor 322, wherein the controller 321 is electrically connected with the signal processor 322, and the controller 321 is electrically connected with the IR cell 318 and the TC cell 320 respectively; and the chamber valve 37, the flush valve 312, the bypass valve 311, the first switching valve 315, the second switching valve 316, the reference valve 310 and the needle valve 314 are all electrically controlled valves and are electrically connected with the controller 321 respectively, and the controller 321 realizes the opening and closing of different gas paths by controlling the opening and closing of different electrically controlled valves so as to realize joint determination modes of different gases.

The intake switching valve 33 and the carrier gas valve 34 are electrically controlled valves and are electrically connected with the controller 321 respectively, and the controller 321 is communicated with different intake tubes by controlling the intake switching valve 33 so as to realize introduction switching of different carrier gases.

The melting and extraction system of the combined oxygen, nitrogen and hydrogen joint determination device based on thermal conductivity-infrared technique provided by the present invention can realize switching of two carrier gases of high-purity $N_2$ and high-purity He by the intake switching valve 33 to provide the corresponding carrier gases for different joint determination modes.

The analytical gas transmission system of the combined oxygen, nitrogen and hydrogen joint determination device based on thermal conductivity-infrared technique provided by the present invention can provide the corresponding gas path flow modes for different joint determination modes, the switching of analytical gas paths is realized through the first switching valve 315, the second switching valve 316 and the MFC, and the switching of different joint determination modes is realized in combination with the converter 317 and the analysis purification reagent tube 319.

The mass flow controller (MFC) in the analytical gas transmission system of the combined oxygen, nitrogen and hydrogen joint determination device based on thermal conductivity-infrared technique provided by the present invention realizes switching of parameter modes of different carrier gases through software control.

The signal detection system of the combined oxygen, nitrogen and hydrogen joint determination device based on thermal conductivity-infrared technique provided by the present invention comprises two determination units: an IR cell and a TC cell which are connected in series through the analysis purification reagent tube 319. The IR cell comprises $CO$, $CO_2$ and $H_2O$ vapor determination channels. The signal detection system of the present invention can realize component determination of different analytical gases in different joint determination modes.

The signal analysis system in the combined oxygen, nitrogen and hydrogen joint determination device based on thermal conductivity-infrared technique provided by the present invention controls the whole analysis process, and flexibly selects different joint determination modes in the method setup to realize switching through one-click operation, so the operation is simple and convenient.

The present invention also provides a combined oxygen, nitrogen and hydrogen joint determination method based on thermal conductivity-infrared technique, which is applied in the above combined oxygen, nitrogen and hydrogen joint determination device based on thermal conductivity-infrared technique, comprising the following steps:

A sample of metal or alloy material is put into the impulse furnace 38 to release oxygen, nitrogen and hydrogen as $CO$, $N_2$ and $H_2$ molecules as analytical gases;

The intake switching valve 33 is controlled to introduce high-purity He or high-purity $N_2$ as a carrier gas;

One branch of the introduced carrier gas enters the TC cell 320 through the reference valve 310 and the needle valve 314 as the reference gas, and the other branch enters the chamber valve 37. When the sample is analyzed in the working state, the carrier gas is blown into the impulse furnace 38 to carry the analytical gas released from the molten sample into the dust filter 39;

The analytical gas passing through the dust filter 39 enters the flush valve 312, and the flush valve 312 is opened at the degassing stage at the beginning of the analysis to exhaust waste gases; and after degassing, the analytical gas containing components to be determined passes through the bypass valve 311 and the mass flowmeter 313 in sequence;

When high-purity He is introduced as the carrier gas, the analytical gas is carried by the carrier gas to enter the IR cell 318 through the first switching valve 315, the converter 317 and the second switching valve 316 in sequence and then enter the TC cell 320 through the analysis purification reagent tube 319 to realize O/N joint determination, N/H joint determination and O/N/H joint determination, wherein oxygen and hydrogen are determined by the IR absorption method, and nitrogen is determined by the TC method;

When high-purity $N_2$ is introduced as the carrier gas, the analytical gas is carried by the carrier gas to enter the IR cell 318 through the second switching valve 316 and then enter the TC cell 320 through the analysis purification reagent tube 319 to realize the O/H joint determination mode, wherein oxygen is determined by the IR absorption method, and hydrogen is determined by the TC method.

Exemplarily, the mass flowmeter 313 is a mass flow controller MFC which adopts an He parameter mode in O/N, N/H and O/N/H joint determination modes and adopts an Ar parameter mode in the O/H joint determination mode.

The specific implementation process is shown in FIG. 3. The sample is put into the impulse furnace 38 from the feeding port, and dropped into the degassed high-temperature crucible for melting, the carrier gas treated by front-end purification passes through the chamber valve 37 and carries analytical gases ($H_2$, CO and $N_2$) released from the sample to pass through the subsequent analytical gas transmission system and signal detection system, and the signal analysis system controls the gas flow paths for joint determination modes of different elements through the software algorithm system, and realizes the integration of O/N, O/H, N/H and O/N/H joint determination on one device through the configuration combination of TC and IR absorption technologies. The TC method can realize determination of nitrogen or hydrogen content in the sample by determination of $N_2$ or $H_2$ in the TC cell 320; and the IR absorption method can realize determination of oxygen or hydrogen content in the sample by determination of $CO/CO_2$ or $H_2O$ vapor in the IR cell 318.

Figure 4:
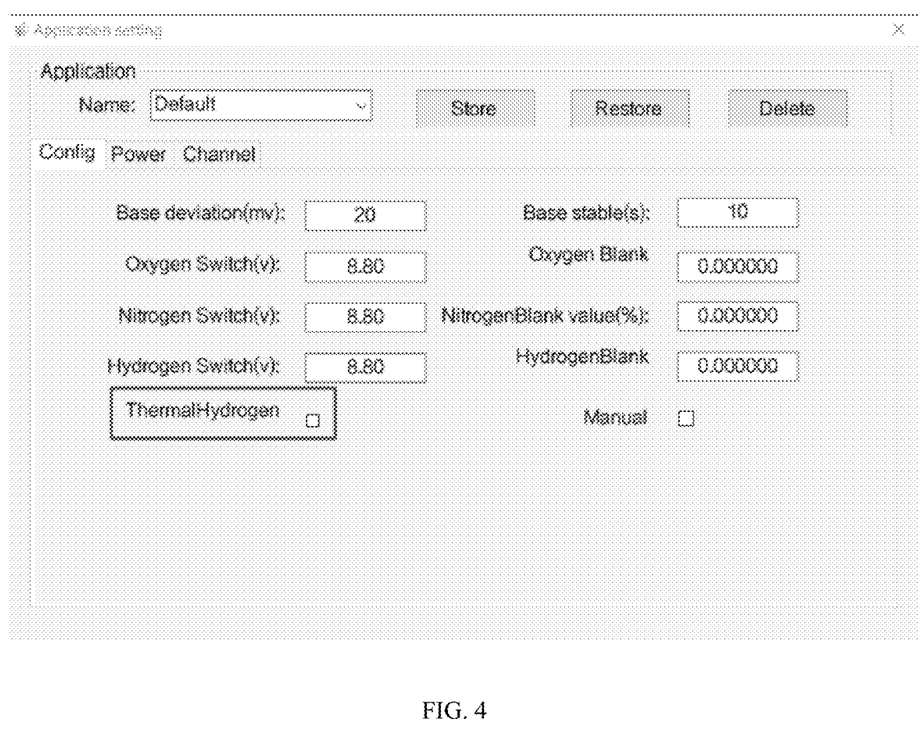
FIG. 4 shows a software control interface of a signal processor provided by the present invention.

Different carrier gases are required in joint determination modes of different elements, for example, for O/H joint determination, high-purity $N_2$ is used as the carrier gas, oxygen is determined by the IR absorption method, and hydrogen is determined by the TC method; and for N/H joint determination, high-purity He is used as the carrier gas, nitrogen is determined by the TC method, and hydrogen is determined by the IR absorption method. When a joint determination mode, such as O/H joint determination, is selected, "hydrogen determination by TC" is selected in the method setup of the software (as shown in FIG. 4), the intake switching valve 33 will automatically switch the connection to high-purity $N_2$, the high-purity $N_2$ flows through the purifying furnace 35 through the carrier has valve 34, and foreign trace gases such as methane and hydrocarbons contained in the carrier gas react with high-temperature (about 500° C.) CuO in the purifying furnace 35 to form $CO_2$ and $H_2O$ which are absorbed and removed by soda asbestos as a carbon dioxide absorbent and dehydrite as a water absorbent in the carrier gas purification reagent tube 36. The chemical reactions that take place are as follows:

The carrier gas further purified is divided into two branches: one branch provides a reference gas for the TC cell 320 through the reference valve 310 and the needle valve 314 (along the path shown by the asterisk line in FIG. 3); and the other branch passes through the carrier gas valve 7, and enters the subsequent gas path through the bypass valve 311 without passing through the impulse furnace 38 (along the path shown by the solid dot line in FIG. 3) in the standby opening state of the instrument so that the subsequent analytical gas path maintains a stable flow in the standby state, so as to ensure the stability of the signal detection system, and passes through the impulse furnace 38 in the kindling state of instrument analysis.

In the analytical gas transmission system, the graphite crucible in the impulse furnace 38 is degassed at high temperature to exhaust foreign gases through the flush valve 312 in the state of instrument analysis. After degassing, the sample is automatically dropped into the high-temperature graphite crucible and melted, and oxygen, nitrogen and hydrogen contained in the sample are converted into CO, $N_2$ and $H_2$ gas molecules which are carried by the carrier gas through the dust filter 39 for dust removal and then flow through the bypass valve 311 and the mass flow controller MFC, and the analysis flow is stable at 400 ml/min.

In the O/H joint determination mode, "hydrogen determination by TC" is selected in the method setup of the software, and the analytical gas flow, along the path shown by the triangular line in FIG. 3, directly enters the second switching valve 316 from the first switching valve 315 and then enters the subsequent signal detection system without passing through the high-temperature converter 317. Meanwhile, the carrier gas is switched to high-purity $N_2$, and the mass flow controller (MFC) is switched to the Ar gas mode. Since the molecular weight of Ar is similar to that of $N_2$, the Ar gas mode of MFC is suitable for high-purity $N_2$.

In the O/N, N/H and O/N/H joint determination modes, "IR hydrogen determination" is defaulted in the method setup of the software, and the analytical gas flow, along the path shown by the hollow dot line in FIG. 3, flows through the high-temperature converter 317 from the first switching valve 315 and then enters the subsequent signal detection system through the second switching valve 316. At this moment, CO and $H_2$ react chemically with CuO in the converter at high temperature (about 500° C.) to form $CO_2$ and $H_2O$ vapor molecules, and nitrogen is still present as $N_2$. The reaction formulas are as follows:

Meanwhile, the carrier gas is switched to high-purity He, and the mass flow controller (MFC) is switched to the He gas mode.

The signal detection system is composed of the IR cell 318, the analysis purification reagent tube 319 and the TC cell 320, wherein the IR cell 318 comprises a $CO_2$ determination channel, a CO determination channel and an $H_2O$ vapor determination channel. In the O/N joint determination mode, high-purity He as the carrier gas carries the formed $CO_2$ and $N_2$ to enter the IR cell 318 and the TC cell 320. The mass percentage of oxygen is calculated according to the absorption peak intensity of the $CO_2$ determination channel in the IR cell 318 at the wavelength of 4.2 μm; and subsequently, $CO_2$ is absorbed by the alkali asbestos in the analysis purification reagent tube 319, leaving only $N_2$ carried by high-purity He into the TC cell 320. The mass percentage of nitrogen is calculated according to the signal difference generated by $N_2$ in the analysis arm of the TC cell 320 and the He carrier gas in the reference arm. In the O/H joint determination mode, high-purity $N_2$ carries the formed CO and $H_2$ to enter the IR cell 318 and the TC cell 320. The mass percentage of oxygen is calculated according to the absorption peak intensity of the CO determination channel in the IR cell 318 at the wavelength of 4.5 μm. The mass percentage of hydrogen is calculated according to the signal difference generated by $H_2$ in the analysis arm of the TC cell 320 and the $N_2$ carrier gas in the reference arm. In the N/H joint determination mode, high-purity He carries the formed $N_2$ and $H_2$ to enter the IR cell 318 and the TC cell 320. The mass percentage of hydrogen is calculated according to the absorption peak intensity of the $H_2O$ vapor determination channel in the IR cell 318 at the wavelength of 6.5 μm. The mass percentage of nitrogen is calculated according to the signal difference generated by $N_2$ in the analysis arm of the TC cell 320 and the He carrier gas in the reference arm. In the O/N/H joint determination mode, high-purity He carries the formed $CO_2$, $N_2$ and $H_2O$ vapor to enter the IR cell 318 and the TC cell 320. The mass percentage of oxygen is calculated according to the absorption peak intensity of the $CO_2$ determination channel in the IR cell 318 at the wavelength of 4.2 μm. The mass percentage of hydrogen is calculated according to the absorption peak intensity of the $H_2O$ vapor determination channel in the IR cell 318 at the wavelength of 6.5 μm. The mass percentage of nitrogen is calculated according to the signal difference generated by $N_2$ in the analysis arm of the TC cell 320 and the He carrier gas in the reference arm.

For hydrogen determination, the determination accuracy and precision of the IR absorption method are not as good as those of the TC method for the ultra-low content range of hydrogen ≤3 μg/g. In addition, if the hydrogen content in the sample is too high and more than 1000 μg/g, $H_2O$ vapor is prone to condensation, resulting in measurement errors, so the IR absorption method is suitable for the determination of hydrogen in the content range of 3 μg/g-1000 μg/g. The TC method can realize full-range determination of hydrogen. Compared with the IR absorption method, the TC method has more advantages for the determination of hydrogen in the range of high content (≥1000 μg/g) and ultra-low content (≤3 μg/g), but has the disadvantage that it is impossible to realize joint determination with oxygen and nitrogen. The user can make flexible choices and configuration according to the actual requirements.

The signal analysis system comprises a controller 321 and a signal processor 322, carries out data processing and signal conversion and controls the whole analysis process. The signal analysis system is used for switching joint determination modes of different elements, switching the carrier gas requirements of joint determination modes of different elements, switching the gas path flows for joint determination modes of different elements, and finally obtaining the sample analysis result according to the signal output of the signal detection system.

By switching the analytical gas path flows and using the front-end sample melting system and the back-end signal detection system in common, the combination of multiple joint determination modes of oxygen, nitrogen and hydrogen is realized on one device, which meets different determination requirements of different users and saves the device cost. The software algorithm system controls the switching of the corresponding solenoid valve and the switching of the carrier gas parameters of the mass flow sensor in different joint determination modes, which is ingenious in design and simple and convenient in operation.

The IR cell comprises CO, $CO_2$ and $H_2O$ vapor determination channels to realize the determination of different analytical gas components.

The IR absorption method for hydrogen determination can realize O/H joint determination and O/N/H joint determination, but is only suitable for the determination of hydrogen in the range of 3 μg/g-1000 μg/g; and the TC method can realize full-range determination of hydrogen and N/H joint determination, and has obvious advantages in determination of hydrogen in high content (≥1000 μg/g) and ultra-low content (≤3 μg/g) compared with the IR absorption method. The present invention integrates the advantages of two hydrogen determination methods on one device to maximize the advantages. The present invention realizes different joint determinations of oxygen, nitrogen and hydrogen on one device, and the user can make flexible choices according to the actual requirements such as the type of elements to be determined and the content range in the production process. The selection and switching of different joint determination modes can be realized through the software algorithm system, and such one-click operation is convenient and fast, which is specially suitable for the determination of oxygen, nitrogen and hydrogen in metal and alloy materials.

The present invention also provides a software system for performing the above combined oxygen, nitrogen and hydrogen joint determination method based on thermal conductivity-infrared technique.

The present invention will be further described below in combination with specific embodiments.

The analysis of a titanium alloy sample is taken as an example. Oxygen, nitrogen and hydrogen are particularly critical to the quality control of titanium alloys and need to be accurately determined, the hydrogen content in titanium alloys is usually in the range of 10 μg/g-200 μg/g, the use of the IR absorption method for hydrogen determination can meet the requirements of the determination range, so the O/N/H joint determination mode is selected.

First, two analytical gases are introduced: high-purity He and high-purity $N_2$. After the instrument in the device is preheated, the analysis software is opened to enter the O/N/H joint determination mode. In the default state, the device uses the IR absorption method to determine hydrogen. At this moment, the controller controls the intake switching valve 33 to switch the carrier gas to high-purity He gas supply mode.

The circulating water is opened, and the power source of the impulse furnace is turned on. The titanium alloy sample is picked up with tweezers and placed on an electronic balance, and about 0.1 g is weighed, which is accurate to 0.1 mg. The sample is wrapped in a nickel basket and placed into the impulse furnace 38 from the feeding port, and the "start" button in the relevant control software is clicked for analysis. The device performs automatic analysis according to the set parameters such as power, time and comparison level.

The carrier gas passes through the carrier gas valve 34 and then passes through the high-temperature purifying furnace 35 and the carrier gas purification reagent tube 36, the carrier gas further purified is injected into the impulse furnace 38 through the chamber valve 37, and the impulse furnace 38 degasses the graphite crucible at a power of about 5.5 KW. The formed foreign gases are emptied through the flush valve 312. After degassing, the sample is dropped into the high-temperature graphite crucible from the feeding mechanism of the impulse furnace 38, oxygen, nitrogen and hydrogen in the sample are respectively carried by the carrier gas in the form of CO, $N_2$ and $H_2$ molecules to pass through the bypass valve 311 and then through the mass flow controller MFC 313; and at this time, the carrier gas parameter of MFC is He gas mode, and the flow rate is always stable at 400 ml/min. In the O/N/H joint determination mode, the gas flow passes through the high-temperature converter 317, and finally, the signal detection system determines $CO_2$ and $H_2O$ vapor components in the analytical gas by the IR cell 318 and determines $N_2$ in the analytical gas by the TC cell 320 to obtain the content of oxygen, nitrogen and hydrogen in the sample.

After analysis, the "open" button in the software is clicked to replace a new graphite crucible. In this way, parallel determination is carried on the sample three times. Appropriate titanium alloy reference materials, with the content range of oxygen, nitrogen and hydrogen covering the content of the sample to be determined, are selected, each reference material is determined according to the above testing process, and a working curve is drawn. Then the analysis result of the titanium alloy sample determined before is selected, "recalculate" is selected in the software menu, and the result bar of the software gives the corrected analysis results of oxygen, nitrogen and hydrogen in the new calibration working curve. It is also possible to determine the reference materials first, establish the working curve, and then determine the sample to be determined. However, in this way, the approximate content range of oxygen, nitrogen and hydrogen in the sample to be determined cannot be understood in advance, and blindness exists in the selection of reference materials. Table 1 shows the determination data of a titanium alloy sample.

TABLE 1

| Sample | Element | Found $\omega$ % | Average $\omega$ % | Standard Deviation SD/% | Relative Standard Deviation RSD/% |
|---|---|---|---|---|---|
| Ti-1 # | O | 0.125, 0.124, 0.121 | 0.123 | 0.0021 | 1.7 |
| | N | 0.0045, 0.0039, 0.0041 | 0.0042 | 0.0003 | 7.3 |
| | H | 0.0182, 0.0179, 0.0176 | 0.0179 | 0.0003 | 1.7 |

In another embodiment, the magnetic Nd—Fe—B alloy material is taken as an example, and the content of oxygen and hydrogen is a required determination item of Nd—Fe—B alloy products. Coarse powder with high hydrogen content which is usually more than 0.1% is prepared by the "hydrogen decrepitation" process in the production process of Nd—Fe—B alloys, the O/H joint determination mode can be used, and the TC method for hydrogen determination is selected in the method setup of the software (as shown in FIG. 4) to avoid errors caused by condensation of $H_2O$ vapor during hydrogen determination with the IR absorption method.

The software will realize the synchronous switching of the intake switching valve 33, the first switching valve 315 and the second switching valve 316 according to the joint determination method to switch the carrier gas to the high-purity $N_2$ gas supply mode. Meanwhile, the carrier gas parameter of the mass flow controller MFC 313 is switched from the He mode to the Ar mode.

The circulating water is opened, and the power source of the impulse furnace is turned on. About 50 mg of sample is weighed on the electronic balance, which is accurate to 0.1 mg, the sample is wrapped with nickel foil and then put into the impulse furnace from the feeding port, and the "start" button in the software is clicked for analysis. The instrument performs automatic analysis according to the set parameters such as power, time and comparison level in the method.

The carrier gas passes through the carrier gas valve 34 and then passes through the high-temperature purifying furnace 35 and the carrier gas purification reagent tube 36, the carrier gas further purified is injected into the impulse furnace 38 through the chamber valve 37, and the impulse furnace 38 degasses the graphite crucible at a power of about 5.5 KW. The formed foreign gases are emptied through the flush valve 12. After degassing, the sample is dropped into the high-temperature graphite crucible from the feeding mechanism of the impulse furnace 38, oxygen, nitrogen and hydrogen in the sample are respectively carried by the carrier gas in the form of CO, $N_2$ and $H_2$ molecules to pass through the bypass valve 311 and then through the mass flow controller MFC 313, and the flow rate is always stable at 400 ml/min. In the O/H joint determination mode, the gas flow does not pass through the high-temperature converter 317, and finally, the signal detection system determines CO in the analytical gas by the IR cell 318 and determines $H_2$ in the analytical gas by the TC cell 320 to obtain the content of oxygen and hydrogen in the sample.

After analysis, the "open" button in the software is clicked to replace a new graphite crucible. The above operation is repeated in this way, and parallel determination is carried on the sample three times. Since no corresponding reference material is available for Nd—Fe—B, other types of metal alloys or powder metallurgy reference materials with similar content of oxygen and hydrogen can only be selected.

Each reference material is determined according to the above testing process, the working curve is drawn, then the analysis result of the Nd—Fe—B alloy sample determined before is selected, "recalculate" is selected in the software menu, and the result bar of the software gives the corrected determination results of oxygen and hydrogen in the new calibration working curve. It is also possible to analyze the reference materials first, establish the working curve, and then analyze the sample to be determined. However, in this way, the approximate content range of oxygen and hydrogen in the sample to be determined cannot be understood in advance, which is not conducive to selecting appropriate reference materials. Table 2 shows the determination data of an Nd—Fe—B sample.

TABLE 2

| Sample | Element | Found $\omega$ % | Average $\omega$ % | Standard Deviation SD/% | Relative Standard Deviation RSD/% |
|---|---|---|---|---|---|
| NdFeB-1# | O | 0.423, 0.417, 0.426 | 0.422 | 0.0046 | 1.1 |
| | H | 0.154, 0.149, 0.156 | 0.153 | 0.0036 | 2.4 |

Specific individual cases are applied herein for elaborating the principle and embodiments of the present invention. The illustration of the above embodiments is merely used for helping to understand the method and the core thought of the present invention. Meanwhile, for those ordinary skilled in the art, specific embodiments and the application scope may be changed in accordance with the thought of the present invention. In conclusion, the contents of the description shall not be interpreted as a limitation to the present invention.

The invention claimed is:

1. A combined oxygen, nitrogen and hydrogen joint determination device based on thermal conductivity-infrared technique, comprising a melting and extraction system, an analytical gas transmission system, a signal detection system and a signal analysis system;

the melting and extraction system comprises a carrier gas introduction pipeline, a chamber valve, an impulse furnace and a dust filter communicated in sequence, wherein the carrier gas introduction pipeline is connected with two intake tubes and configured for introducing different carrier gases, the carrier gas introduction pipeline comprises an intake switching valve, a carrier gas valve, a purifying furnace and a carrier gas purification reagent tube connected in sequence, the carrier gas purification reagent tube is in fluid communication with the chamber valve, and the intake switching valve is connected with two intake tubes and configured for introducing different carrier gases; and the two intake tubes are respectively a first air tube and a second air tube, and high-purity He is introduced into the first air tube as a carrier gas, and high-purity N2 is introduced into the second air tube as a carrier gas;

the analytical gas transmission system comprises a flush valve, a bypass valve, a mass flowmeter and a first switching valve communicated in sequence, wherein the flush valve is in fluid communication with the dust filter, the bypass valve is in fluid communication with the chamber valve, the first switching valve is respectively connected with a converter and a second switching valve, the converter is in fluid communication with the second switching valve, the analytical gas transmission system also comprises a reference valve and a needle valve, the reference valve is in fluid communication with the chamber valve, and the needle valve is in fluid communication with the reference valve;

the signal detection system comprises an infrared (IR) cell, an analysis purification reagent tube and a thermal conductivity (TC) cell communicated in sequence, wherein the IR cell is in fluid communication with the second switching valve, and the TC cell is in fluid communication with the needle valve;

the signal analysis system comprises a controller and a processor, wherein the controller is electrically connected with the processor, and the controller is electrically connected with the IR cell and the TC cell respectively; and the chamber valve, the flush valve, the bypass valve, the first switching valve, the second switching valve, the reference valve and the needle valve are all electrically controlled valves and are electrically connected with the controller respectively, and the controller is configured to the open and close the different gas paths by controlling the opening and closing of the different electrically controlled valves so as to realize joint determination modes of different gases.

2. The combined oxygen, nitrogen and hydrogen joint determination device based on thermal conductivity-infrared technique according to claim 1, wherein the intake tube is provided with a pressure relief valve.

3. The combined oxygen, nitrogen and hydrogen joint determination device based on thermal conductivity-infrared technique according to claim 1, wherein the intake switching valve and the carrier gas valve are electrically controlled valves and are electrically connected with the controller respectively, and the controller is in fluid communication with different intake tubes to control the intake switching valve so as to realize introduction switching of different carrier gases.

4. A combined oxygen, nitrogen and hydrogen joint determination method based on thermal conductivity-infrared technique, which is applied in the combined oxygen, nitrogen and hydrogen joint determination device based on thermal conductivity-infrared technique of claim 1, comprising the following steps: a sample of metal or alloy material is put into the impulse furnace and configured to release oxygen, nitrogen and hydrogen as CO, N2 and H2 molecules as analytical gases;

the carrier gas introduction pipeline is controlled to introduce high-purity He or high-purity N2 as a carrier gas; one branch of the introduced carrier gas enters the TC cell through the reference valve and the needle valve as the reference gas, and the other branch enters the chamber valve;

then as the sample is analyzed in the working state, the carrier gas is blown into the impulse furnace to carry the analytical gas released from the molten sample into the dust filter; and the analytical gas passing through the dust filter enters the flush valve, and the flush valve is opened at the degassing stage at the beginning of the analysis to exhaust waste gases; and after degassing, the analytical gas containing components to be determined passes through the bypass valve and the mass flowmeter in sequence; when high-purity He is introduced as the carrier gas, the analytical gas is carried by the carrier gas to enter the IR cell through the first switching valve, the converter and the second switching valve in sequence and then enter the TC cell through the analysis purification reagent tube to realize O/N joint determination, N/H joint determination and O/N/H joint determination, wherein oxygen and hydrogen are determined by the IR absorption method, and nitrogen is determined by the TC method; when high-purity N2 is introduced as the carrier gas, the analytical gas is carried by the carrier gas to enter the IR cell through the second switching valve and then enter the TC cell through the analysis purification reagent tube to realize the O/H joint determination mode, wherein oxygen is determined by the IR absorption method, and hydrogen is determined by the TC method.

5. A combined oxygen, nitrogen and hydrogen joint determination method based on thermal conductivity-infrared technique, which is applied in the combined oxygen, nitrogen and hydrogen joint determination device based on thermal conductivity-infrared technique of claim 2, comprising the following steps:

a sample of metal or alloy material is put into the impulse furnace to release oxygen, nitrogen and hydrogen as CO, $N_2$ and $H_2$ molecules as analytical gases;

the carrier gas introduction pipeline is controlled to introduce high-purity He or high-purity $N_2$ as a carrier gas;

one branch of the introduced carrier gas enters the TC cell through the reference valve and the needle valve as the reference gas, and the other branch enters the chamber valve, when the sample is analyzed in the working state, the carrier gas is blown into the impulse furnace to carry the analytical gas released from the molten sample into the dust filter;

the analytical gas passing through the dust filter enters the flush valve, and the flush valve is opened at the degassing stage at the beginning of the analysis to exhaust waste gases; and after degassing, the analytical gas containing components to be determined passes through the bypass valve and the mass flowmeter in sequence;

when high-purity He is introduced as the carrier gas, the analytical gas is carried by the carrier gas to enter the IR cell through the first switching valve, the converter and the second switching valve in sequence and then enter the TC cell through the analysis purification reagent tube to realize O/N joint determination, N/H joint determination and O/N/H joint determination, wherein oxygen and hydrogen are determined by the IR absorption method, and nitrogen is determined by the TC method;

when high-purity $N_2$ is introduced as the carrier gas, the analytical gas is carried by the carrier gas to enter the IR cell through the second switching valve and then enter the TC cell through the analysis purification reagent tube to realize the O/H joint determination mode, wherein oxygen is determined by the IR absorption method, and hydrogen is determined by the TC method.

6. The combined oxygen, nitrogen and hydrogen joint determination method based on thermal conductivity-infrared technique according to claim 4, wherein the mass flowmeter is a mass flow controller MFC which adopts an He parameter mode in O/N, N/H and O/N/H joint determination modes and adopts an N parameter mode in the O/H joint determination mode.

* * * * *